(12) United States Patent
Teague et al.

(10) Patent No.: US 8,540,729 B2
(45) Date of Patent: *Sep. 24, 2013

(54) TREATMENT AND REMOVAL OF OBJECTS IN ANATOMICAL LUMENS

(75) Inventors: James Teague, Spencer, IN (US); James Riley, Bloomington, IN (US); Todd Sloan, Medway, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 554 days.

This patent is subject to a terminal disclaimer.

(21) Appl. No.: 12/003,963

(22) Filed: Jan. 3, 2008

(65) Prior Publication Data

US 2008/0177276 A1    Jul. 24, 2008

Related U.S. Application Data

(63) Continuation of application No. 10/820,050, filed on Apr. 8, 2004, now Pat. No. 7,338,501, which is a continuation of application No. 10/052,899, filed on Jan. 16, 2002, now Pat. No. 6,740,096.

(51) Int. Cl.
*A61B 17/22* (2006.01)
*A61M 29/00* (2006.01)

(52) U.S. Cl.
USPC .......................................... 606/127; 606/200

(58) Field of Classification Search
USPC .......................................... 606/114, 127, 200
See application file for complete search history.

(56) References Cited

U.S. PATENT DOCUMENTS

| | | | |
|---|---|---|---|
| 4,003,369 A | 1/1977 | Heilman et al. | |
| 4,080,706 A | 3/1978 | Heilman et al. | |
| 4,706,671 A | 11/1987 | Weinrib | |
| 4,724,846 A | 2/1988 | Evans, III | |
| 4,813,925 A | 3/1989 | Anderson et al. | |
| 4,957,479 A | 9/1990 | Roemer | |
| 5,054,501 A | 10/1991 | Chuttani et al. | |
| 5,122,154 A | 6/1992 | Rhodes | |
| 5,379,779 A * | 1/1995 | Rowland et al. | 600/585 |
| 5,514,176 A | 5/1996 | Bosley, Jr. | |
| 5,562,641 A | 10/1996 | Flomenblit et al. | |

(Continued)

FOREIGN PATENT DOCUMENTS

| | | |
|---|---|---|
| EP | 1064888 | 3/2001 |
| EP | 1208816 | 5/2002 |

(Continued)

OTHER PUBLICATIONS

International Search Report for PCT/US03/00195 dated Apr. 28, 2003.

*Primary Examiner* — Gary Jackson
*Assistant Examiner* — Michael Mendoza
(74) *Attorney, Agent, or Firm* — Bookoff McAndrews, PLLC (57) ABSTRACT

A medical device can be used to entrain biological or foreign material during a medical procedure for the fragmentation of the material. The device also can be used to remove the material safely from the body. The device has a core element with a first portion extending substantially longitudinally and a second portion wound to form at least a helical coil in the shape of cone. A flat wire can substantially wrap the first and second portions of the core element, or a wire can substantially wrap the first portion and a sheath can substantially cover the second portion.

15 Claims, 7 Drawing Sheets

(56) References Cited

U.S. PATENT DOCUMENTS

| | | |
|---|---|---|
| 5,647,843 A | 7/1997 | Mesrobian et al. |
| 5,681,274 A | 10/1997 | Perkins et al. |
| 5,795,319 A | 8/1998 | Ali |
| 5,843,176 A | 12/1998 | Weier |
| 5,962,007 A | 10/1999 | Cooper et al. |
| 5,964,744 A | 10/1999 | Balbierz et al. |
| 6,019,779 A | 2/2000 | Thorud et al. |
| 6,027,516 A | 2/2000 | Kolobow et al. |
| 6,093,199 A | 7/2000 | Brown et al. |
| 6,113,621 A | 9/2000 | Wiktor |
| 6,174,305 B1 | 1/2001 | Mikus et al. |
| 6,214,042 B1 | 4/2001 | Jocobsen et al. |
| 6,248,113 B1 | 6/2001 | Fina |
| 6,258,098 B1 | 7/2001 | Taylor et al. |
| 6,290,721 B1 | 9/2001 | Heath |
| 6,436,112 B2 | 8/2002 | Wensel et al. |
| 2001/0031971 A1 | 10/2001 | Dretler et al. |
| 2001/0031980 A1 | 10/2001 | Wensel et al. |

FOREIGN PATENT DOCUMENTS

| | | |
|---|---|---|
| WO | WO 97/06357 | 3/1994 |
| WO | WO/9406357 | 3/1994 |
| WO | WO 97/27808 | 8/1997 |
| WO | WO 98/25656 | 6/1998 |
| WO | WO 99/23958 | 5/1999 |
| WO | WO 01/01869 | 1/2001 |

\* cited by examiner

TREATMENT AND REMOVAL OF OBJECTS IN ANATOMICAL LUMENS

This is a continuation application of U.S. patent application No. 10/820,050, now U.S. Pat. No. 7,338,501, filed Apr. 8, 2004, which is a continuation application of U.S. patent application Ser. No. 10/052,899, now U.S. Pat. No. 6,740,096, filed Jan. 16, 2002, the entirety of which are incorporated herein by reference.

TECHNICAL FIELD

This invention relates to medical treatments of objects within anatomical lumens of the body, and more specifically, to devices and methods for entraining and extracting such objects from within the body.

BACKGROUND INFORMATION

Concretions can develop in certain parts of the body, such as in the kidneys, pancreas, and gallbladder. Minimally invasive medical procedures generally involve causing limited trauma to the tissues of a patient, and can be used to dispose of problematic concretions. Lithotripsy and ureteroscopy, for example, are used to treat urinary calculi (e.g., kidney stones) in the ureter of patients.

Lithotripsy is a medical procedure that uses energy in various forms such as acoustic shock waves, pneumatic pulsation, electrical hydraulic shock waves, or laser beams to break up biological concretions such as urinary calculi (e.g., kidney stones). The force of the energy, when applied either extracorporeally or intracorporeally, usually in focused and continuous or successive bursts, comminutes a kidney stone into smaller fragments that may be extracted from the body or allowed to pass through urination. With the help of imaging tools such as transureteroscopic video technology and fluoroscopic imaging, the operator of the lithotripter device can monitor the progress of the medical procedure and terminate treatment when residual fragments are small enough to be voided or removed.

Intracorporeal fragmentation of urinary calculi can prove problematic in that stones and/or stone fragments in the ureter may become repositioned closer to and possibly migrate back toward the kidney, thereby requiring further medical intervention to prevent the aggravation of the patient's condition. It is desirable to be able to extract such fragments from the body using a single instrument, to prevent the need for successive instrumentation.

Many known stone extraction devices are rigid and lack the maneuverability and flexibility to engage and disengage repeatedly a stone without harming the surrounding tissue. For example, if a stone is still too large to be extracted without further fragmentation, it can be difficult to disengage the stone from such an extraction device without damaging the delicate lining of the ureteral wall.

SUMMARY OF THE INVENTION

The present invention mitigates the risk of damage to surrounding body tissue when treating and/or removing organic material (e.g., blood clots, tissue, and biological concretions such as urinary, biliary, and pancreatic stones) and inorganic material (e.g., components of a medical device or other foreign matter), which may obstruct or otherwise be present within the body's anatomical lumens. In one embodiment, the invention prevents the upward migration of stone fragments generated during a stone fragmentation procedure and safely and efficiently extracts fragments from the body. The invention also enables repeated application to stones, stone fragments, and other biological and nonbiological/foreign material while minimizing trauma to the surrounding tissue.

A medical device, in accordance with an embodiment of the invention, comprises a core element made at least partially of a shape-memory material. Shape-memory material is a material that can be formed into a particular shape, retain that shape during resting conditions (e.g., when the shaped material is in free space or when external forces applied to the shaped material are insufficient to substantially deform the shape), be deformed into a second shape upon subjecting the initial shape to a sufficiently strong external force, and revert substantially back to the initial shape once the external force is no longer applied. Examples of shape memory material include synthetic plastics, stainless steel, and superelastic, metallic alloys of nickel/titanium (commonly referred to as nitinol), copper, cobalt, vanadium, chromium, iron, or the like. In one embodiment, a first portion of the core element extends substantially longitudinally, and a second portion is wound to form a helical coil. The helical coil is adapted to taper from a larger diameter at a proximal end thereof to a smaller diameter at a distal end thereof, thereby resembling a helical cone shape.

In one embodiment, a flat wire (with, for example, a square, rectangular, or other quadrilateral cross-section) substantially wraps the first and second portions of the core element. A distal end of the flat wire can be attached to the distal end of the helical coil, so as to maintain the relative orientation and position between the flat wire and the core element. In a further embodiment, a layer of polymeric material substantially covers the entire outer surface of the flat wire (i.e., the surface of the flat wire that contacts the walls of the anatomical lumen or catheter), including that portion of the flat wire that wraps both the first and second portions of the core element. In another embodiment, the polymeric layer covers a portion of the outer surface of the flat wire wrapping the second portion of the core element, while leaving the outer surface of the flat wire wrapping the first longitudinal portion of the core element uncovered. Alternatively, the polymeric layer covers the outer surface of the flat wire wrapped about the second portion of the core element and at least a portion of the first longitudinal section in the vicinity of the helical cone.

In another embodiment, a wire element substantially wraps only the first longitudinal portion of the core element, and a sheath (of, for example, a polymeric material) covers the second, helical cone portion of the core element. The proximal end of the sheath can be attached to the distal end of the wire element, and the distal end of the sheath can be attached to the distal end of the second portion of the core element.

In yet another embodiment, the curved, second portion of the core element is covered substantially by a polymeric material and the longitudinal section of the core element remains uncovered. In this embodiment, the core element is not covered by a wire element.

In one embodiment, the polymeric material/layer is applied by spraying. For example, a polymeric material can be spray-coated onto the outer surface of the wire and/or directly onto the helical cone section of the core element. In another embodiment, the polymeric material can be a sheath that is heat-shrunk about the wire and/or the second portion of the core element. The polymeric sheath can be made of PTFE, EPTFE, ETFE or other suitable material that exhibits a light color capable of reflecting most of the laser energy used during a lithotripsy procedure and absorbing or dissipating the energy not reflected with no or minimal damage to the polymeric sheath at normal laser operating levels.

The polymeric sheath preferably comprises a plurality of colors along a length of the sheath in order to assist the physician who is performing the lithotripsy procedure to detect movement in the sheath and to assist in gauging distances. In this manner, the physician can determine not only when the second portion of the core element (corresponding to the curved or helical cone section of the core element) is deployed/expanded, but also the configuration of the core element during various phases of the lithotripsy procedure. In one embodiment, the polymeric sheath exhibits the standard color of a PTFE heat shrink extrusion with a colored stripe along the length of the sheath. As the medical device is manipulated, the relative size and distances of the wound sections of the helical coil can be readily determined by examining the spiral configuration of the colored stripe, which appears about the wound section of the core element. The striped color is also preferably selected to be resistant to and reflect laser energy so as to minimize damage to the polymeric sheath.

The helical cone is adapted to ensnare objects of various sizes from within an anatomical lumen, e.g., a kidney stone from within a ureter. Superelastic properties of the helical cone can enable it to unwind and assume a substantially linear configuration upon being subjected to a pulling force along a longitudinal axis of the core element, such as when the helical cone is pulled within a catheter adapted to receive the core element, the wire, and the polymeric sheath. The cone can be pulled into an outer catheter when a captured stone or other object is too large to pass through the anatomical lumen without further fragmentation or other treatment. The helical cone substantially rewinds into its helical cone rest state when released and unrestrained by such a force.

The substantially linear configuration of the helical cone when positioned within the catheter enables the catheter to retain a small diameter, which facilitates the placement of the catheter beyond the object in the anatomical lumen. Once the catheter is properly positioned, the second portion of the core element is pushed out of the distal end of the catheter where the helical cone substantially rewinds or expands back into*its tapered configuration. As discussed, the helical cone can be reversibly transformed into a substantially linear configuration when drawn into the catheter so that it can be repeatably positioned and deployed in more advantageous locations.

In yet another aspect, the second portion of the core element forms one or more curved shapes in addition to the helical cone, such as another helical cone or a single loop. The single loop or curved element can be located near the proximal end of the helical cone in order to assist in the manipulation, extraction, or repositioning of the kidney stone or other object in the anatomical lumen. The second helical cone can be located near the distal end of the first helical cone so that if the first helical cone unwinds and is pulled into the catheter when a kidney stone or other object is too large to pass through the anatomical lumen, the second helical cone can serve as a backstop during the subsequent treatment procedure without having to redeploy the first helical cone.

Regardless of the particular curved element employed, the curved element can be made of or include superelastic/shape-memory material that enables the deformation and reformation of the curved element as described above in connection with the helical cone. Similarly, the curved element can be wrapped entirely by a wire element, such as round or flat wire, or can be covered by a polymeric material as described above in connection with the helical cone. Those skilled in the art will recognize that the various wire wrapping and polymeric covering embodiments previously discussed in connection with the helical cone can be used as well for the curved element. The wire wrapping and polymeric covering techniques can also be common or different as between the curved element and the helical cone. For example, the first longitudinal portion of the core element can be wrapped in flat wire, while the curved element and helical cone are covered by a polymeric sheath. Alternatively, the first longitudinal portion of the core element can be uncovered, while the shaped portion(s) of the core element are covered with a polymeric sheath, which can comprise a plurality of laser resistant colors.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead being placed upon illustrating the principles of the invention.

DESCRIPTION

Figure 1A:
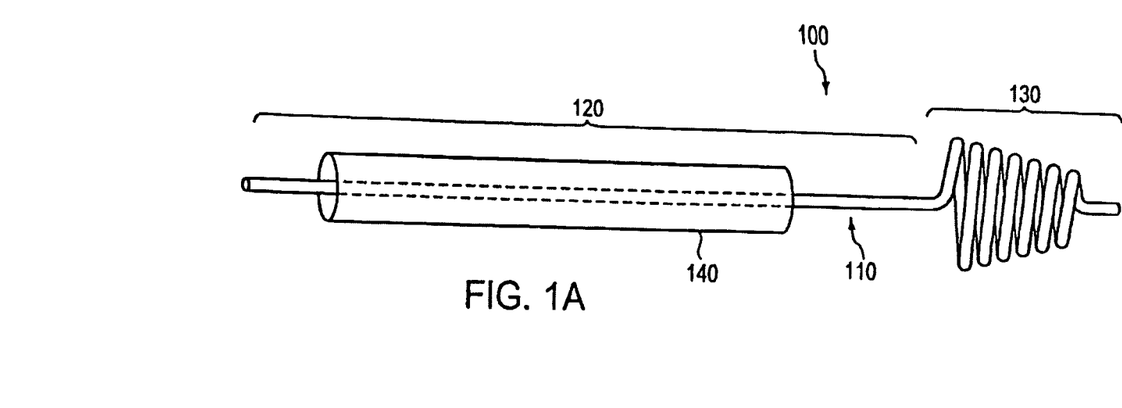
FIG. 1A provides a profile view of a medical device in accordance with an embodiment of the invention, in which the helical cone of the device is shown in a deployed position.
Figure 1B:
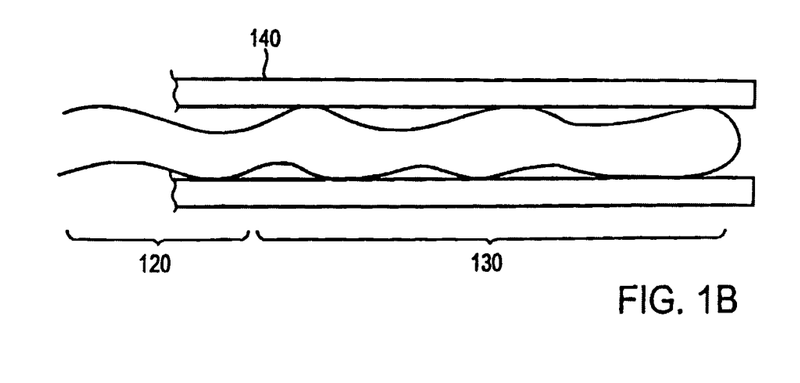
FIG. 1B provides a profile view of the medical device of FIG. 1A, with the helical cone pulled into a catheter.

With reference to FIGS. 1A and 1B, a medical device 100, in accordance with an embodiment of the invention, is configured to support the treatment and/or removal of organic material (e.g., blood clots, tissue, and biological concretions such as urinary, biliary, and pancreatic stones) and inorganic material (e.g., components of a medical device or other foreign matter) from within an anatomical lumen. The medical device 100 comprises a catheter 140, and a core element 110 with a substantially longitudinal section 120 and a second section wound to form a helical coil 130, wherein the helical coil 130 preferably tapers from a larger diameter at a proximal-end thereof to a smaller diameter at a distal end thereof, thereby resembling a helical cone. The core element 110 is preferably constructed, at least in part, of a shape-memory material that enables the core element 110 to assume the helical cone configuration during resting conditions (e.g., when the core element 110 is in free space or when external forces applied to the core element 110 are insufficient to substantially deform the helical cone configuration), such as when the the helical coil 130 is deployed from the catheter 140 into the anatomical lumen as shown in FIG. 1A. The shape-memory material of the helical coil 130 also enables the helical coil 130 to assume a substantially linear configuration when drawn into the catheter 140, as shown in FIG. 1B, without significantly affecting the ability of the helical coil 130 to revert back into the helical cone configuration when later deployed. Shape-memory materials suitable for use in forming the core element 110 include synthetic plastics, stainless steel, and metallic alloys of nickel, titanium, coper, cobalt, vanadium, chromium, and iron. In one embodiment, the shape-memory material forming the core element 110 is preferably a superelastic material such as nitinol, which is a nickel-titanium alloy.

Figure 2:
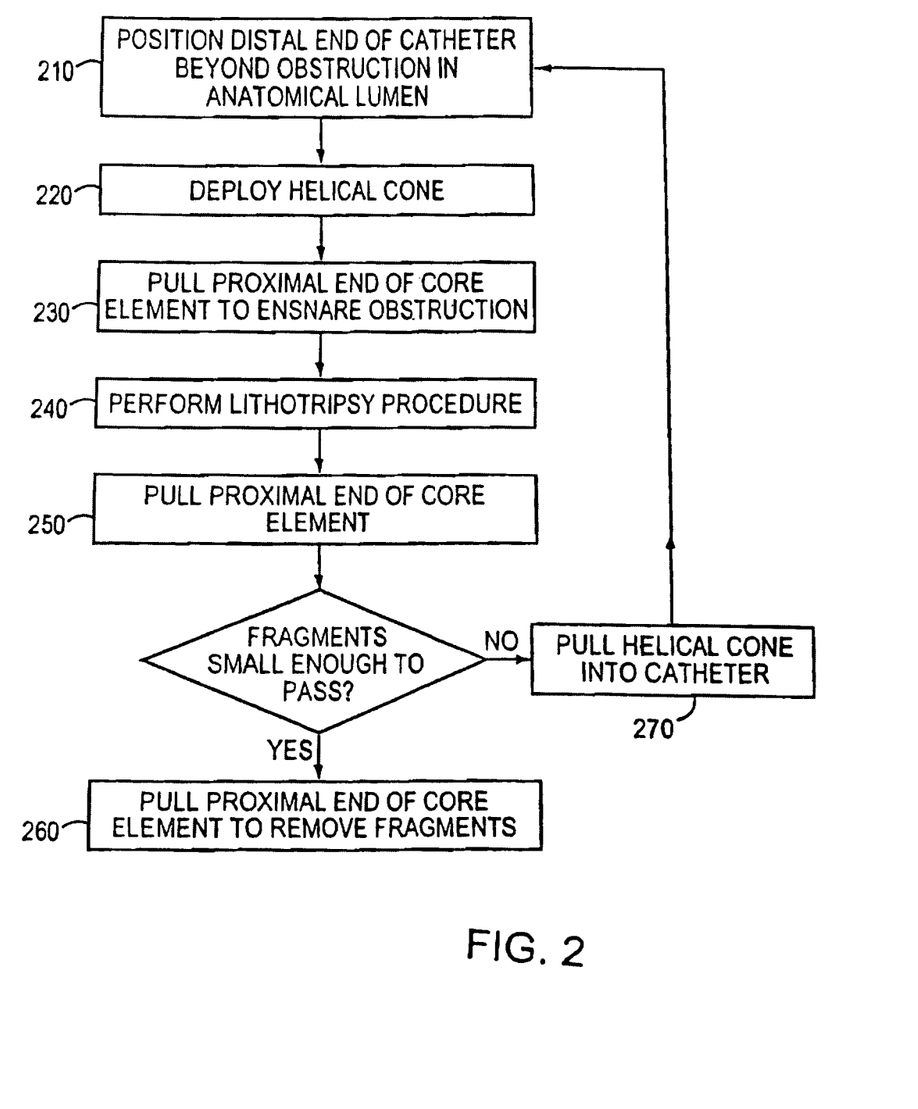
FIG. 2 is a flow diagram illustrating the use of the medical device of FIG. 1A for removing objects from anatomical lumens.

In operation and with reference to FIG. 2, a health practitioner inserts the medical device 100, with the helical coil 130 retracted into its unwound or substantially linear configuration within the catheter 140 (as shown in FIG. 1B), into the anatomical lumen (not shown) until a distal end of the catheter 140 is positioned beyond an object in the anatomical lumen (step 210). For example, in a lithotripsy procedure to remove a kidney stone from a patient's ureter, the catheter 140 is introduced into the patient's urinary passage until a radiopaque distal portion of the catheter 140 (the position of which can be viewed by the health practitioner) passes beyond the location of the stone lodged in the ureter. The health practitioner then deploys the helical coil 130 in the vicinity of a distal end of the obstruction by exerting a pushing force along the longitudinal axis of the core element 110 (step 220).

As the helical coil 130 is released from the confined space of the catheter 140, the helical coil 130 reforms into the helical cone configuration illustrated in FIG. 1A and occludes the anatomical lumen. Preferably the larger diameter of the helical coil-130 is sized to be substantially the same as or slightly greater than that of the anatomical lumen so that the passage will be sufficiently occluded and prevent any subsequent migration of the kidney stone.

With the helical coil 130 in its deployed position and the catheter drawn back away from the obstruction, the health practitioner can exert a pulling force along the longitudinal axis of the core element 110 in order to ensnare the stone within the helical coil 130 (step 230). At this point, a lithotripsy procedure is performed to fragment the stone into smaller fragments (step 240). The helical coil 130 serves as a physical barrier or back-stop during the lithotripsy procedure to ensure that the smaller fragments do not migrate in an undesired direction, e.g., kidney stone fragments migrating back toward the kidney. The superelasticity of the helical coil 130 coupled with its conical configuration, provides a flexible barrier that is able to absorb the kinetic energy of the fragments produced when a laser or other energy is used to comminute or ablate the obstruction. The instrumentation used to perform the lithotripsy can be introduced into the desired location adjacent to the stone using a second lumen within the catheter 140 or via another catheter or guidewire.

Once the lithotripsy procedure is complete, the health practitioner can exert a pulling force along the longitudinal axis of the core element 110 in order to ensnare the fragments (step 250). If the fragments are small enough to pass through the anatomical lumen, then the health practitioner can drag the fragments from the anatomical lumen and out of the body (step 260). However, if the fragments are still too large to pass through sections of the anatomical lumen, then the pulling force exerted along the longitudinal axis of the core element 110 while the curved surfaces of the helical coil 130 engage the immovable fragment, causes the helical coil 130 to unwind and to be subsequently pulled into the catheter 140 (step 270). In this scenario, the health practitioner can repeat the treatment procedure by redeploying the helical coil 130 beyond the stone (steps 210-230) and performing a second lithotripsy procedure to further fragment the remaining obstructions.

The overall length of the medical device 100 (and thus that of core element 110), depends on the application for which the medical device 100 is intended. Generally the overall length will be n the range of about 50 to about 250 cm. In one embodiment and with respect to urinary applications, the total length of the device 100 is about 140-220 cm, and preferably about 200 cm. Devices for other applications, or those intended for use with children, will be of different lengths.

The particular number of turns, the maximum diameter, and the length of the tapered helical coil 130 depend, again, on the intended use of the device 100. In one embodiment, the helical coil 130 has between about 5 and 15 turns, and preferably about 7 to 10 turns. Its maximum diameter, at the proximal end of the helical coil 130 can be, for example, in the range of about 0.2 cm to 3.0 cm, and preferably is about 0.7-0.8 cm. The overall length of the helical coil 130 depends on the size of the core element 110 and on the number of turns, and in one embodiment is in the range of about 0.5 cm to about 3.0 cm and preferably about 1.5 cm. Adjacent turns of the tapered helical coil 130 may abut each other or be separated by small gaps (e.g., up to about 2 mm wide) as illustrated in FIG. 1A.

Figure 3:
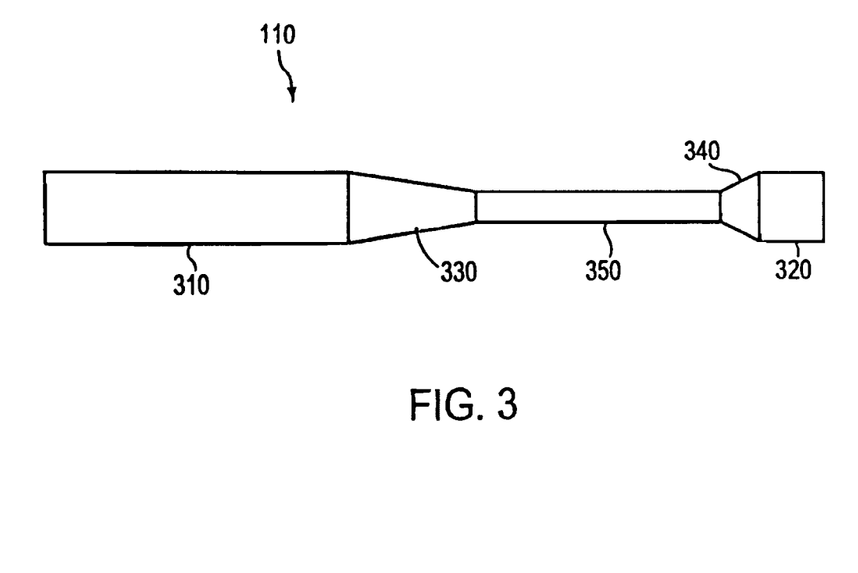
FIG. 3 is a profile view of the tapered, wire core of the medical device of FIG. 1A.

In one embodiment and with reference to FIG. 3, at least a portion of the core element 110 forming the helical coil 130 is tapered exhibiting, for example, a maximum 5 diameter of about 0.020 inches and being made from a superelastic material such as a NiTiCr alloy (e.g., 55.73% Ni, 44.04% Ti, 0.22% Cr, and less than 0.05% C and O). As shown, the core element 110 in its substantially linear configuration has been ground so that, in addition to full diameter sections 310 and 320 adjacent, respectively, its distal and proximal ends, it includes a pair of tapered portions 330, 340 on opposite sides of a smaller diameter portion 350. The long full diameter section 310 extending from the proximal end of the core element 110, and the longer tapered portion 330, provide desired column strength in the portion of the core element 110 proximal of the smaller diameter portion 350. The long full diameter section 310 has a length of, for example, about 130-200 cm, and preferably about 150 cm and a diameter of about 0.02 inches. The smaller diameter portion 350 has a length of, for example, about 20-40 cm, and preferably about 30 cm and a diameter of about 0.009 inches. The longer tapered portion 330 is, for example, about 5-10 cm in length, and preferably about 8 cm, and the shorter tapered portion 340 has a length of, for example, about 0.01 to 0.05 inches, and preferably 0.025 inches. The shorter full diameter section 320 has a length of, for example, about 0.1 to 0.5 inches, and about 0.2 inches in one embodiment, thereby enabling the medical device 100 to access the renal pelvis area of the kidney. In one embodiment, the entire core element 110 can be a continuous piece of superelastic wire. In other embodiments, the smaller diameter portion 350 of the core element 110 forms the helical coil 130 and is made from a superelastic material, while other portions of the core element 110, e.g., the full diameter sections 310, 320 and tapered portions 330, 340, are stainless steel.

The helical cone shape of the helical coil 130 is formed by wrapping the smaller diameter portion 350 of the core element 110 around a mandrel to form it into the desired conical shape, and then applying heat at a particular temperature and for a particular duration in order for the superelastic material of the smaller diameter portion 350 to assume and retain the conical shape when the mandrel and heat treatment are removed. As is known to those skilled in the art, once the smaller diameter portion 350 of the core element 110 has been heat-treated to set the desired helical cone configuration, the helical coil 130 may be drastically, deformed (e.g., by pulling the portions of the core element 110 on either side of the helical coil 130 to straighten the turns forming the helical coil 130) but will return to its set helical cone configuration when released.

Figure 4A:
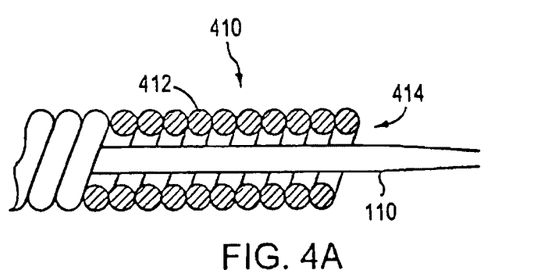
FIG. 4A is a profile view of a wire-wrapping configuration around the wire core of FIG. 3, using a wire with a round cross-section.

In one embodiment and with reference to FIG. 4A, a wire element 410 is helically wrapped around at least a portion of the core element 110 so as to improve the maneuverability of the device 110 when traversing a tortuous anatomical lumen and when deploying and retracting the helical coil 130. In one embodiment, the wire element 410 is a round wire 412.(i.e., has a circular or round cross-section) that covers substantially the entire length of the core element 110. In another embodiment, such as that disclosed in International Publication Number WO 01/01869, which is hereby incorporated by reference in its entirety, the wire element 410 comprises two separate round wires that are coupled to each other and to the core element 110, wherein the diameter of the two wires differs so as to provide greater flexibility in the vicinity of the helical coil 130 without losing column strength in the longitudinal section 120 of the core element 110.

Figure 4B:
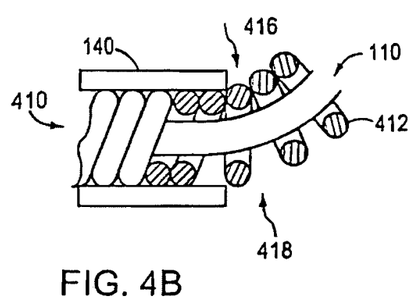
FIG. 4B schematically illustrates the interference and gaps encountered when pulling the round wire of FIG. 4A into the catheter of the medical device.

With reference to FIG. 4B, the round wire 412 of the wire element 410 presents a relatively large surface contact area with respect to surrounding structures and is thus prone to catching the leading edge 416 of the catheter 140 particularly when the helical coil 130 is pulled back into the catheter 140. This difficulty in movement/maneuverability is particularly acute for that portion of the wire element 410 that surrounds the turns of the helical coil 130 because this is the location where the turns of the helically wound wire element are more likely to separate (see, for example, the gap 418 in FIG. 4B). As an illustration, consider the situation where the helical coil 130 ensnares a large concretion in the ureter that is too large to pass through a stricture in the anatomical lumen. In this scenario, the pulling force exerted on the core element 110 will cause the helical coil 130 to unwind and retract into the catheter. The relatively large surface area of the round wire 412 that surrounds the turns of the helical coil 130 inhibits the passage of the core element 110 and surrounding wire element 410 between the already tight space between the concretion and the ureteral wall. The friction from this greater surface area is also more likely to be abrasive to the delicate tissues of the ureter.

Figure 4C:
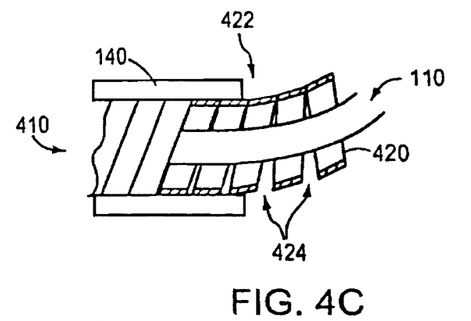
FIG. 4C schematically illustrates how the interference and gaps encountered when pulling the helical cone of FIG. 1A into the catheter is minimized by using a flat wire in accordance with an embodiment of the invention.
Figure 5A:
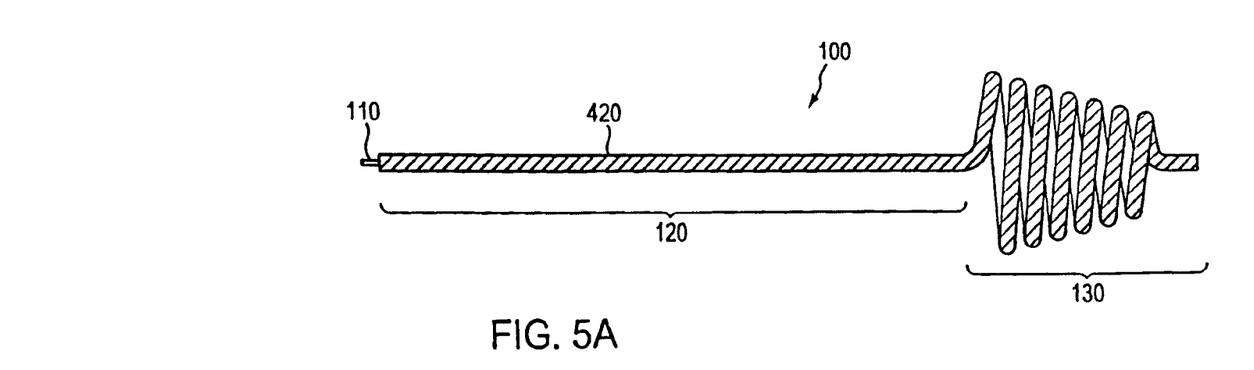
FIG. 5A schematically illustrates that the medical device of FIG. 1A can be wrapped by flat wire along substantially all of its length.

In another embodiment and with reference to FIGS. 4C and 5A, the wire element 410 is made of flat wire 420, preferably with a square cross-section, which presents a smaller profile interface than the round wire 412 of FIG. 4B. The flat wire can alternatively exhibit other quadrilateral cross-sections, such as rectangular or wedge shaped configurations. The smaller profile of the flat wire 420 is less likely to catch the leading edge 422 of the catheter 140 and the gap 424 between the coils of the flat wire 420 are minimized. The decreased surface area of the flat wire 420 improves not only the maneuverability of the device 100 when deploying and retracting the helical coil 130 out of/into the catheter 140, but also presents a smaller risk of damaging the delicate tissue of the ureter when passing by a trapped stone when a restriction in the anatomical lumen is encountered.

In a further embodiment, an outer surface of the flat wire 420 is covered by a low-friction material, such as a fluorinated polymer (e.g., polytetrafluoroethylene), which may be spray coated onto the flat wire 420. Alternatively, a polymer sheath can be heat-shrinked about the flat wire 420. In either case the polymer reduces the amount of friction between the turns of the helical coil 130 and the catheter 130 or object in a restricted anatomical lumen, thereby decreasing the risk of damage to delicate tissues in the surrounding area. In yet another embodiment, the polymer sheath can be applied to directly surround the core element 110 along substantially its entire length, when a wire element 410 is not used.

Figure 4D:
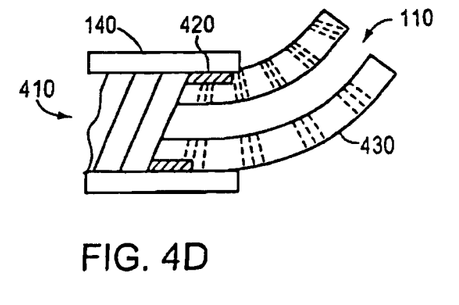
FIG. 4D schematically illustrates how the flat wire of FIG. 4C is coupled to a polymeric sleeve to eliminate substantially interference and gaps while retaining proper strength to manipulate the medical device of FIG. 1A, in accordance with an embodiment of the invention.
Figure 5B:
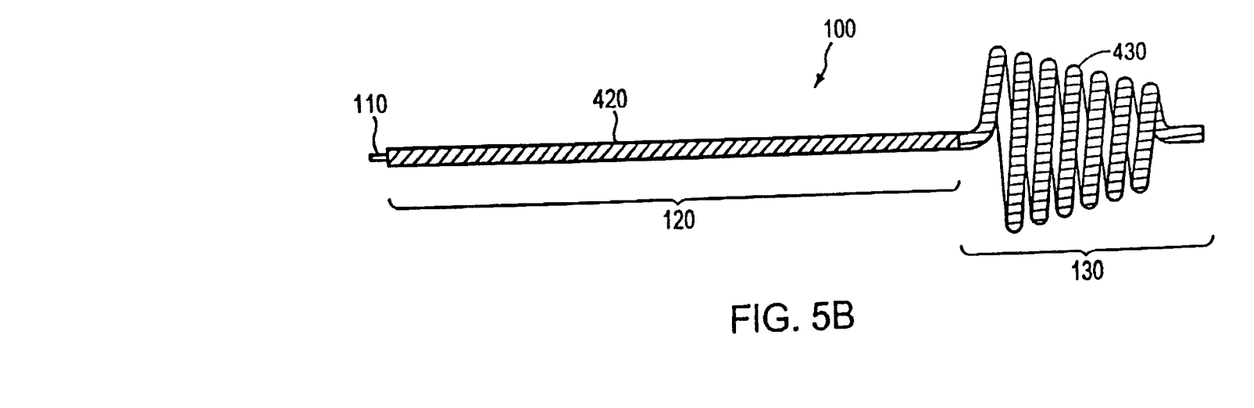
FIG. 5B schematically illustrates that a longitudinal portion of the medical device of FIG. 1A is wrapped with flat wire while the helical cone section of the device is covered by a polymeric sheath, in accordance with an embodiment of the invention.

In another embodiment and with reference to FIGS. 4D and 5B, the flat wire 420 of the wire element 410 substantially wraps only a portion of the core element 110, preferably the longitudinal section 120 (FIG. 1A), and a polymer sheath 430 substantially covers the helical coil 130 section of the core element 110. As discussed above, the polymer sheath 430 can be heat-shrinked about the core element 110 in the region substantially including the helical coil 130. In this manner, the flat wire 420 minimizes the friction associated with pushing/pulling the longitudinal section 120 of the core element 110 by the leading edge of the catheter 140 or by the object in a restricted lumen and retains column strength, while enabling the polymer sheath to slip beyond the catheter edge and the object with substantially minimal friction in an area of the helical coil 130 where friction, and thus damage to surrounding tissue, is most-likely-to-occur.

Figure 6:
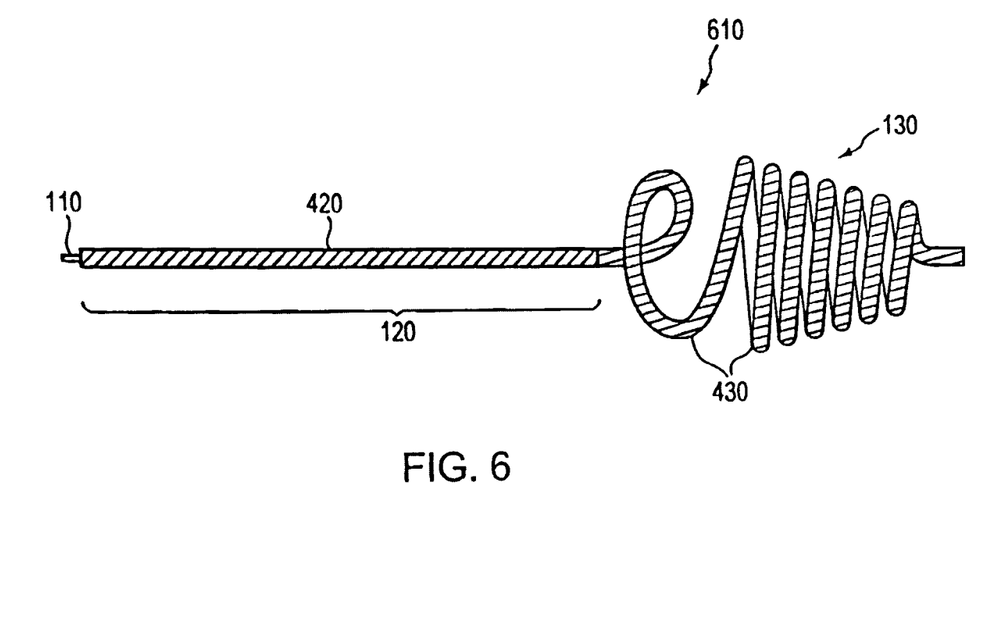
FIG. 6 illustrates that the medical device of FIG. 1A can be adapted to form a plurality of shapes, including a curved element and a helical cone, wherein the plurality of shapes are covered by a polymeric sheath and the longitudinal section is wrapped with flat wire.

With reference to FIG. 6, the core element 110 can form a plurality of shapes including, for example, the helical coil 130 and a curved element 610. In one embodiment, the curved element 610 is a single loop located proximally to the helical coil 130. In one aspect, the curved element 610 is deployed from the catheter 140 after the helical coil 130 has ensnared the object in the anatomical lumen and serves as a cap to maintain the object's relative position within the helical coil 130 for easy removal and further manipulation. The curved element 610 can be wrapped with round wire, flat wire, or any other cross-section of wire, similar to that which wraps the longitudinal section 120 of the core element 110. Alternatively or in conjunction, the curved element 610 can be covered by the same polymeric sheath 430 as that which covers the helical coil 130 or the curved element 610 can be covered by a different polymeric sheath. The curved element 610 can also be covered with a polymeric material that has a different color or other different properties than that of the polymeric material which covers the helical coil 130.

The polymeric material/sheath 430 discussed above can be made of PTFE, EPTFE, ETFE or other suitable material that exhibits laser resistant characteristics (e.g., light color) that prevents or minimizes damage to the core element 110 or other elements of the medical device 100 during a lithotripsy procedure. In one embodiment, the light color of the polymeric sheath 430 surrounding the helical coil 130 differs from the color of other portions of the polymeric sheath 430 that do not surround the helical coil 130 and from the color of other elements of the device 100 in order to assist a health care practitioner in determining whether the tapered helical coil 130 is within or without the-catheter 140 during a lithotripsy procedure. For example, the polymeric material covering the helical coil 130 can be a different color from the catheter 140 or other polymeric material that may cover the longitudinal section 120 of the core element 110. In this manner, when the helical coil 130 has been retracted into the catheter 140, the colored polymer indicates to the health care practitioner that the helical coil 130 has assumed a substantially linear configuration as compared to the helical cone configuration when the helical coil 130 is deployed.

Figure 7:
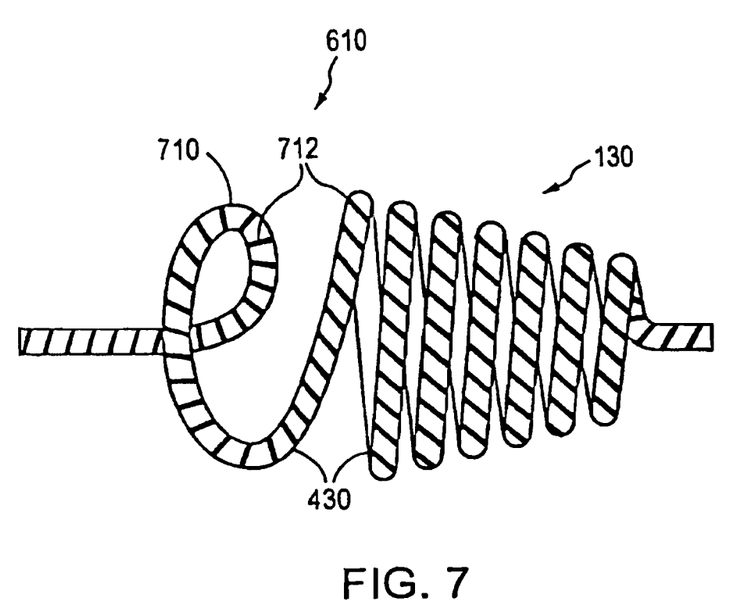
FIG. 7 illustrates that the polymeric sheath covering the curved element and helical cone includes a plurality of colors along a length thereof, in accordance with an embodiment of the invention.

In one embodiment and with reference to FIG. 7, the polymeric sheath 430 preferably comprises a plurality of colors 710, 712 along its length in order to assist the health care practitioner who is performing the lithotripsy procedure to detect movement in the sheath 430 and to assist in gauging distances. In this manner, the health care practitioner can determine not only when the helical coil 130 is deployed/expanded, but also the configuration of the core element 110 during various phases of the lithotripsy procedure. In one embodiment, the polymeric sheath 430 exhibits the standard color 710 of a PTFE heat shrink extrusion with a colored stripe 712 along the length of the sheath. In one embodiment, the colored stripe 712 traverses helically along the length of the sheath 430, while in other embodiments, the colored stripe 712 is positioned medially along the longitudinal axis of the sheath 430 or in accordance with other geometries. In another embodiment, the colored stripe 712 appears in only particular sections of the sheath 430, such as along that portion of the sheath 430 covering the distal end of the device 100. As the medical device 100 is manipulated, the relative size and distances of the wound sections of the helical coil 130 can be readily determined by examining the spiral configuration of the colored stripe 712, which appears about the helical coil 130 the striped color is also preferably selected to be resistant to and reflect laser energy so as to minimize damage to the polymeric sheath 430.

Variations, modifications, and other implementations of what is described and shown herein will occur to those of ordinary skill in the art without departing from the spirit and scope of the invention. The invention is not to be defined only by the preceding illustrative description or drawings.

The invention claimed is:

1. A medical device comprising:
    an elongate sleeve defining a lumen extending longitudinally within at least a portion of the elongate sleeve;
    an elongate core slidably disposable within the lumen, the core having a distal portion capable of transforming between an unrestrained configuration forming a plurality of coils disposed in a conical shape and a restrained configuration forming a substantially linear shape, wherein the distal portion, in the unrestrained configuration, extends from a proximal end of the plurality of coils to a distal end of the elongate core;
    wherein the distal portion of the elongate core includes a coating having a plurality of colors including a first color different from that of the sleeve,
    wherein the elongate core includes a proximal portion that extends proximally from the proximal end of the plurality of coils to a proximal end of the elongate core, the proximal portion including a coating having a second color that is different than the first color of the coating covering the distal portion of the elongate core,
    wherein the second color extends proximally of a proximal end of the sleeve when the entire distal portion extends distally of a distal end of the sleeve, when the entire distal portion is disposed within the sleeve, and when the distal end of the core is positioned proximal to the distal end of the sleeve, and
    wherein the proximal portion has at least one loop in an unrestrained configuration, the configured to assist in maintaining an object within the plurality of coils and is located at a distance from the proximal end of the coils that is substantially greater than a distance between adjacent turns of the coils.

2. The medical device of claim 1, wherein the proximal portion has a substantially linear shape in an unrestrained configuration.

3. The medical device of claim 1, wherein the coating of the proximal portion and the coating of the distal portion comprises one of PTFE, EPTFE, ETFE, or a combination thereof.

4. The medical device of claim 1, wherein the distal portion includes a helical stripe.

5. A medical device comprising:
    an elongate sleeve defining a lumen extending longitudinally within at least a portion of the elongate sleeve; and
    an elongate core formed at least in part of nickel-titanium alloy and slidably disposable within the lumen, the core having a distal portion capable of transforming between an unrestrained configuration forming between 5 and 15 coils disposed in a conical shape and a restrained configuration forming a substantially linear shape;
    wherein adjacent turns of the coil are separated by a space less than 2 mm, wherein the distal portion, in the unrestrained configuration, extends from a proximal end of the coil to a distal end of the elongate core,
    wherein the distal portion of the core includes a coating having a plurality of colors including a longitudinally extending stripe of a first color,
    wherein the elongate core includes a proximal portion that extends proximally from the proximal end of the coils to a proximal end of the elongate core, the proximal portion including a coating having a second color that is different than the first color of the coating of the distal portion of the elongate core,
    wherein the second color extends proximally of a proximal end of the sleeve when the entire distal portion extends distally of a distal end of the sleeve, when the entire distal portion is disposed within the sleeve, and when the distal end of the core is positioned proximally of the distal end of the sleeve;
    wherein the proximal portion has a shape comprised of at least one loop in an unrestrained configuration, and wherein the configured to assist in maintaining an object within the plurality of coils and is located at a distance from the proximal end of the coils that is substantially greater than a distance between adjacent turns of the coils.

6. The medical device of claim 5, wherein the proximal portion has a substantially linear shape in an unrestrained configuration.

7. The medical device of claim 5, wherein the coating of the proximal portion and the coating of the distal portion comprise one of PTFE, EPTFE, ETFE, or a combination thereof.

8. The medical device of claim 5, wherein the coating of the distal portion and the coating of the proximal portion are resistant to laser energy.

9. The medical device of claim 5, wherein the longitudinally extending stripe extends along the entire distal portion.

10. The medical device of claim 5, wherein the longitudinally extending stripe includes a helical stripe.

11. A medical device comprising:
an elongate sleeve defining a lumen extending longitudinally within at least a portion of the elongate sleeve; and
an elongate member slidably disposable within the lumen, the member having a distal portion capable of transforming between an unrestrained configuration forming a plurality of coils disposed in a conical shape and a restrained configuration forming a substantially linear shape;
the distal portion, in the unrestrained configuration, extends from a proximalmost end of the plurality of curved elements to a distal end of the elongate member;
the distal portion including a sheath having a plurality of colors along a length of the sheath such that the plurality of colors exist at a common longitudinal position along the sheath;
the elongate member includes a proximal portion that extends proximally from the distal portion to a proximal end of the elongate member, the proximal portion including a substantially linear shaped portion in an unrestrained configuration; and
wherein the proximal portion further includes at least one loop in an unsrestrained configuration, the configured to assist in maintaining an object within the plurality of coils and is located at a distance from the proximal end of the coils that is substantially greater than a distance between adjacent turns of the coils.

12. The medical device of claim 11, wherein the plurality of colors that exist at a common longitudinal position of the sheath includes at least one longitudinally extending stripe.

13. The medical device of claim 12, wherein the stripe reflects laser energy.

14. The medical device of claim 12, wherein the stripe extends in a helical configuration along a length of the sheath.

15. The medical device of claim 11, wherein the plurality of colors that exist at a common longitudinal position of the sheath includes a stripe, the stripe extending over the entire distal portion, and not extending over the entire proximal portion.

* * * * *

UNITED STATES PATENT AND TRADEMARK OFFICE
CERTIFICATE OF CORRECTION

| | | |
|---|---|---|
| PATENT NO. | : 8,540,729 B2 | Page 1 of 1 |
| APPLICATION NO. | : 12/003963 | |
| DATED | : September 24, 2013 | |
| INVENTOR(S) | : James Teague et al. | |

It is certified that error appears in the above-identified patent and that said Letters Patent is hereby corrected as shown below:

In the Claims

Claim 1, Col. 10, Line 6, --at least one loop is-- is inserted after "the."

Claim 5, Col. 10, Line 50, --at least one loop is-- is inserted after "the."

Claim 11, Col. 12, Line 2, --at least one loop is-- is inserted after "the."

Signed and Sealed this
Twenty-ninth Day of April, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,540,729 B2 | Page 1 of 1 |
| APPLICATION NO. | : 12/003963 | |
| DATED | : September 24, 2013 | |
| INVENTOR(S) | : James Teague et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 681 days.

Signed and Sealed this
Twenty-fourth Day of February, 2015

Michelle K. Lee
*Deputy Director of the United States Patent and Trademark Office*